United States Patent [19]
Vilasi

[11] 3,968,800
[45] July 13, 1976

[54] DEVICE FOR INSERTION INTO A BODY OPENING

[76] Inventor: Joseph A. Vilasi, 37 Wagon Wheel Lane, Dix Hills, N.Y. 11746

[22] Filed: Sept. 17, 1974

[21] Appl. No.: 506,683

[52] U.S. Cl. ............................... 128/343; 128/345; 128/351
[51] Int. Cl.² ................ A61M 29/00; A61M 16/00
[58] Field of Search ........... 128/242, 243, 244, 343, 128/345, 351

[56] References Cited
UNITED STATES PATENTS

| | | |
|---|---|---|
| 832,201 | 10/1906 | Kistler.................................. 128/244 |
| 1,267,066 | 5/1918 | Flack .............................. 128/345 X |
| 1,632,541 | 6/1927 | Cortes................................. 128/244 |
| 3,039,462 | 6/1962 | Walden et al.................. 128/345 X |
| 3,169,529 | 2/1965 | Koenig............................ 128/345 X |

*Primary Examiner*—Channingg L. Pace
*Attorney, Agent, or Firm*—Bauer, Amer & King

[57] ABSTRACT

An essentially hollow device for use in a body opening without limitation to but as an endotracheal tube, a bronchoscope, a vascular or cervical dilator and the like wherein the same has an outer surface that is operable to expand into engagement with the wall of the body opening into which the same is adapted to be inserted.

20 Claims, 9 Drawing Figures

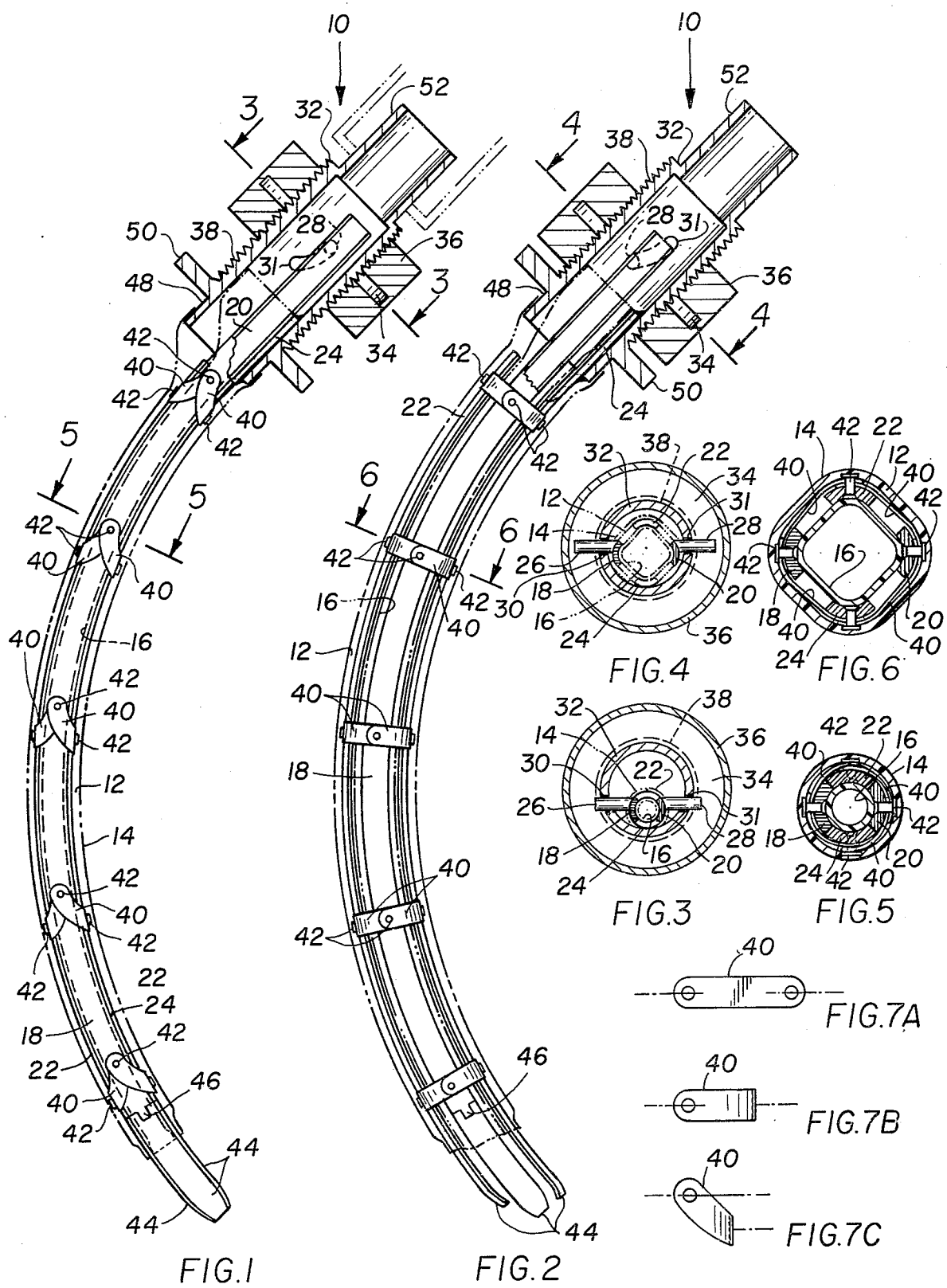

DEVICE FOR INSERTION INTO A BODY OPENING

BACKGROUND OF THE INVENTION

This invention relates to such essentially hollow devices as endotracheal tubes, bronchoscopes, vascular and cervical dilators and the like that are adapted for removable insertion into a body opening. Although reference is made hereinafter to the term "tube", the same is intended to include essentially hollow members that may be of circular cross sectional configuration or of any other cross sectional configuration.

For more convenient explanation and understanding, reference will hereafter be made to endotracheal tubes as illustrative of the prresent invention. An endotracheal tube is used in anesthesiology by inserting the same into the patient orotracheally or nasotracheally below the glottic wall or into the trachea via a tracheostomy opening. At present, a cuff on the exterior of the tube surface is caused to expand into engagement with the trachea below the glottic wall. The cuff is usually formed as a separate sleeve on the tube exterior and is operated by the anesthetist to afford air-tight engagement with the vocal chords to affect an air-tight passage through which the anesthesiologist maintains full and essential control over the patient's ventilation. No leak between the tube and trachea should be tolerated. Hence, the air-tight connection is essential during endotracheal anesthesia.

Prior to the present invention, the endotracheal tube, being elongated, was fixed in internal and external size or cross section along the plane taken substantially perpendicular to the tube length. The tube outer diameter selected by the anesthesiologist most nearly approximated a dimension slightly inferior to or smaller than that of the patient's glottic airway. Thus, tube interior and exterior size was usually fixed. To compensate for the differences between the glottic airway and the tube selected by the anesthesiologist, the cuff on the tube exterior and distal end was inflated in the hope and expectation that it would substitute for the inaccuracy of fit between the endotracheal tube and the larger glottic airway.

Although such cuffs sometimes do close off the space between the tube and the glottic airway, they are an added obstruction to the smooth insertion of the tube into the trachea and constitute an obstruction on an otherwise smooth tube exterior that tends to lacerate the tender tissues during insertion and removal of the tube. Such prior known cuffs have also been known to leak, to rupture when expanded and even to slide or slip off the tube while still in the patient. All of these defects and problems may cause severe and sometimes fatal injury or even require repetition of the intubation procedure or the application of dangerous drugs to the patient.

SUMMARY OF THE INVENTION

Because the prior devices used for endotracheal insertion and other similar purposes are of fixed size, a large number of different size devices must be inventoried to accommodate pediatric and adult patients, each of varying size and age. Accordingly, an object of this invention is to provide an essentially hollow device for use in a body opening in which the same may be operated to assume different sizes and in which the external and internal surfaces may be varied in size such that its interior passage also may be increased and decreased as desired.

Another object of the invention is to eliminate the fixed size tube and its restrictive cuff along with the attendant problems and difficulties the same produce and present.

Still a further object and feature of the invention is to provide an expandable essentially hollow device for removable insertion into a body opening that is subject to the finite control of the user without fear of attendant damage to the patient, and one that is simple to operate and functions easily and readily in accordance with the selective operation made by the user.

The above description, as well as further objects, features and advantages of the present invention, will be more fully appreciated by reference to the following detailed description of a presently preferred, but nonetheless illustrative, embodiment in accordance with the present invention when taken in conjunction with the accompanying drawings wherein:

FIG. 1 is a vertical cross section of a device constructed according to the invention for use as an endotracheal tube showing the same in its full contracted condition;

FIG. 2 is a vertical cross section showing the device in its expanded condition;

FIG. 3 is a cross section of FIG. 1 taken along line 3—3;

FIG. 4 is a cross section of FIG. 2 taken along line 4—4;

FIG. 5 is a cross section of FIG. 1 taken along line 5—5;

FIG. 6 is a cross section of FIG. 2 taken along line 6—6;

FIG. 7A shows a development of an operating link;

FIG. 7B shows the side view of the operating link in its expanding position, and FIG. 7C shows the operating link in its contracted position.

Referring now to the drawing, the device there shown is generally identified by the numeral 10. As indicated previously, for convenience of understanding the present invention, reference will be made to an endotracheal tube. However, it is to be understood that the use of the device need not be specifically limited thereto. Thus, the device 10 is shown in the form of an endotracheal tube and the use thereof will be described with respect to its use as an endotracheal tube. It is believed that those skilled in the art will readily recognize that as the description proceeds, such device 10 may be utilized also for convenient insertion into and removal from any other body opening.

The device 10 comprises a tube-like elongated member 12 having an essentially hollow interior adapted to function as the substitute for the glottic airway when inserted into the patient and properly expanded according to the teaching of the invention. The tube member 12 is preferably made from an elastomeric material such as rubber, soft plastic and the like enabling it to expand to and from an original formed configuration in response to selective operation in a manner to be described.

The member 12, therefore, is provided with an outer surface 14 that is relatively smooth and uninterrupted along its usable length so as to enable the same to be non-abrasively inserted into and removed from the selected body opening. The interior of the member 12 is also provided with an inner surface 16 that is smooth and uninterrupted and, therefore, relatively free of obstructions that in any way interfere with the rapid flow of gases along the passage or obstruct a view through such passage. Although the inner and outer surfaces 14 and 16 form the member 12, initially they may be formed as a single or unitary structure. However, for convenience of understanding and for ease of explanation, and without constituting a limitation upon the scope of the invention, the surfaces 14 and 16 are illustrated as being two separate and distinct structures.

Included within the device 10 are a plurality of movable means which include a plurality of elongated legs 18 and 20 that are substantially in opposed relationship to each other and legs 22 and 24 that are similarly in opposed relationship with respect to each other and spaced alternately between legs 18 and 20. The legs 18 to 24 may be made from metal, plastic, rubber or any other suitable material that will enable the same to maintain a rigidity of their own to support the tube-like member 12 in any desired contour along its length. However, such legs may be of such material as to enable them to be flexed and to be deformed along their lengths to conform to the curvature of the length of the opening into which the device 10 is adapted to be inserted. Thus, where the device 10 is utilized as a bronchoscope, it may be desirable to eliminate the long curve of the member 12 as illustrated in FIGS. 1 and 2. When the legs 18 to 24 are made of a deformable material with sufficient rigidity to maintain the shape into which they are bent by the user, the device 10 may be easily converted from an endotracheal tube to a bronchoscope or for use in any other body opening.

The legs extend for a substantial length of the member 12 and terminate at the upper or proximal end in various positions. For example, again for convenience of understanding, four legs are illustrated. As the description proceeds, those skilled in the art will recognize that the number of legs illustrated is not controlling upon the scope of the invention. Any number may be utilized to effect the end result sought. In the present disclosure, the oppositely disposed legs 18 and 20 extend beyond the length of the adjacent intermediate legs 22 and 24 for connection with actuator pins 26 and 28 which are guided in curved slots 30 and 31 formed within a sleeve 32.

The ends of the pins 26 and 28 remote from their connections with the legs 18 and 20 are mounted within an annular groove 34 of a manually rotatable actuator 36 that may be selectively operated by the user of the device 10. The annular groove 34 is within the interior of the rotatable actuator 36 so that no portion of the same is exposed to contamination by the surrounding atmosphere. The actuator 36 has an internal thread that mates with an external thread 38 on the sleeve 32 to provide for simple threaded relative adjustment of the actuator 36 with respect to the sleeve 32. The length of the thread 38 is sufficient to enable the pins 26 to travel for the full length of their respective curved guide slots 30 and 31 with the threaded travel of the actuator 36 being similarly restricted by the length of the slots. One of the movable means, more specifically the leg 24, is fixed or secured to the interior surface of the sleeve 32 in the manner shown in FIGS. 1 and 2 while the opposite leg 22 is substantially freely movable in the respect that it is not fixed to any part of the sleeve or its attendant structure.

Included as part of the movable means are translation elements or means in the form of links 40. The links 40 are illustrated in FIG. 7A in their flat initially developed form to show their configuration as initially manufactured. FIG. 7C illustrates the appearance of the links 40 in their collapsed condition as shown in the collapsed position of the device 10 in FIG. 1, while FIG. 7B illustrates the appearance of the links 40 in their expanded operative position as illustrated in FIG. 2. There are a plurality of sets of the translation means comprising the links 40, each relatively spaced along the length of the movable legs 18 to 24.

In the drawing, five sets of such translation means are shown. Once again, it should be noted that the particular number of sets of translation means shown should not constitute a limitation upon the scope of the invention since any number may be used depending upon the length of the device 10 and the degree of operation of expansion and contraction that is required. However, an explanation of one set of translation link means should suffice for all. In this regard, each set comprises four such links 40. A set of four links fully encompasses the legs 18 to 24. In the particular arrangement illustrated, each leg pivotally supports two links at a common hinge rivet or pin 42 as shown more clearly in FIG. 6.

Although the links are illustrated as riveted and hingedly moved to the outer surfaces of the legs, it is within the contemplation of the invention that the same may be pivotally mounted to the inner surfaces of such legs with equal facility. To enable the links to perform their desired functions, they, too, may be made from the same material as the legs 18 to 24 with sufficient rigidity to retain their shape but also sufficient flexibility to enable the same to flex from the bent shape illustrated in FIG. 7C to the expanded shape of that illustrated in FIG. 7B.

The cross section contour of each of the legs 18 to 24 is curved in order to effect a curved outer configuration and similarly shaped cross section of the tube member 12 when the same is in its collapsed or contracted condition of FIG. 1 and moved toward and into its expanded condition of FIG. 2. Naturally, by increasing the number of such legs, it will be easier to effect a more circular cross sectional appearance of the outer and inner surfaces 14 and 16 of the member 12. If it is desired to effect an oval cross section in the tube member 12, the cross section contour of the legs will be correspondingly formed. However, again for convenience of understanding and explanation of the invention, only four legs have been shown. Therefore, when the device 10 is in its collapsed condition as illustrated om FIGS. 1, 3 and 5, the cross section of the outer and inner surfaces 14 and 16 is fully circular while the cross section of FIGS. 2, 4 and 6 in the expanded condition approximates or is substantially circular.

To effect the expansion of the tube member 12 from its normal contracted condition as shown in FIGS. 1, 3 and 5, the sleeve 32 is held in a stationary position. The actuator 36 is rotated by threading the same downwardly along the length of the thread 38. This causes the pins 26 and 28 to move with the operated actuator 36 downwardly and in an arcuate manner guided along the length of their respective curved slots 30 and 31. Depending upon the extent of operation of the actuator collar 36, the pins 26 and 28 will cause the legs 18 and 20 to move relative to the fixed leg 24 and the free leg 22 by urging the pivots 42 of the translation means downward in the direction toward the distal end of the device 10.

As the pivots 42 are moved downward, they effect a straightening of the pivotally connected links 40 from their positions as shown in FIG. 1 toward their extreme expanded positions shown in FIG. 2, thereby causing an expansion of the member 12 from the position of FIG. 1 to that of FIG. 2. It has been found that when the member 12 is made from an elastomeric material that has a memory tending to return the same to its initial formed or normally contracted condition, as the collar 36 is rotated in the reverse direction along the thread 38, the member 12 will apply a contracting force to the legs and the translation means so as to cause the same to return toward their initial starting position and normally retract the cross section size of the tube to its normal condition.

When the device 10 is utilized as an endotracheal tube, it may be provided at its distal or entry end with additional more flexible deformable tips 44 conveniently secured to the distal ends of each of the legs 18, 20, 22 and 24 by a locking tongue and groove arrangement as shown at 46 or by any other convenient securing means. The remote or proximal ends of the tips 44 will be held within the distal end of the member 12, either to extend therebeyond as shown in the drawing or to be confined therewithin in the same manner as are the legs 18 to 24.

To aid in understanding, the tips 44 are shown extended beyond the distal end of the tube member 12. When the tips 44 are made of an easily deformable material, they may be readily shaped by the anesthetist or surgeon to the configuration and contour of the opening into which the same are to be inserted so as to enable their ready and easy insertion into and removal from such opening. Because each of the tips 44 is connected to a respective leg, they define a continuation and extension of each such leg. Moreover, because each of the tips and their connection with their respective legs is well within the confines of the member 12, it is impossible for the same to become dislodged within the body opening into which they are adapted to be inserted.

The remote or proximal end of the tube member 12 is securely mounted in an air-tight non-contaminating manner to an extension 48 of the sleeve 32. To provide for an air-tight device, the connection of the tube 12 with the sleeve 32 maintains the air-tight integrity of the overall device to enable the admission of gases into the body opening in accordance with the requirements of the user and the needs of the patient. A flange 50 provided adjacent the lower end of the sleeve 32 may serve as a stop for the actuation of the collar 36. It may also function as a collar means for the user to manually grasp or lock the same to retain the sleeve from unwanted rotation. The proximal extension 52 of the sleeve 32 may be used to attach the device 10 to the necessary attendant gas lines of anesthetic equipment when the device is used as an endotracheal tube or it may be used to support the same to other attendant equipment and structure when the device 10 is utilized for other purposes.

Thus, in operation when the device 10 is used as an endotracheal tube, the legs 18 to 24 will be bent into the elongated curved shape as shown in FIG. 1 to approximate the elongated contour of the trachea into which the same is adapted to be inserted. The tips 44 may be further deformed and shaped by the anesthetist to assure their smooth and easy entry into the glottic passageway. The smooth outer surface 14 of the device assures the gliding insertion of the member 12 into the glottic airway without tearing or lacerating the tender tissues.

When once the device is properly positioned within the airway, the anesthetist need merely rotate the collar 36 with respect to the sleeve 32 in the manner previously described to cause the expansion of the outer surface 14 until such time as the outer surface 14 airtightly and snugly engages with the wall of the glottic airway to close the same. By connecting the inner surface 16 with the legs 18 to 24 and also the translation means 40 and 42, the inner surface 16 will similarly enlarge or expand in cross section to provide an enlarged passageway to assure the full supply of the proper gases to the patient.

Further, by enclosing the operable means including the translation means within the confines of the member 12 between the outer and inner surfaces 14 and 16 thereof, should any of the operable means rupture or break during any time of use of the device within the patient, there need be no fear upon the part of the user or the patient that the broken element will become dislodged within the patient because the details thereof are completely encompassed within such tube member 12. If the member 12 is made of a translucent or transparent material, the anesthetist or surgeon using the same may frequently inspect the device 10 to assure himself that the parts are in proper working order before the same is used.

Thus, the present invention provides a device that has a smooth uninterrupted exterior and interior surface, each of which is capable of expansion and contraction for engagement with the walls of the body opening into which the same is adapted to be inserted.

While there have been shown and described and pointed out the fundamental novel features of the invention as applied to a preferred embodiment thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:

1. A device for insertion into a body opening comprising a tube-like member longer in length than in cross section having an uninterrupted relatively smooth outer surface yieldable to vary in cross section along substantially its full length, a hollow passage extending through the full length of said member, means movable in response to a selective operation to vary the cross section of the outer surface of said member along substantially the full length thereof, and operable means connected with said movable means to selectively move the same to vary the cross section of said outer surface of said member.

2. A device as in claim 1, said passage being open at the opposite ends of said member, and said member having an interior surface defining said passage, said interior surface being movable with said movable means to vary the cross section of the passage.

3. A device as in claim 1, said movable means including at least two relatively movable elements in which one of said elements is connected with said operable means to move said one element relative to the other, and translation means to move said elements relative to each other in the direction of the cross section of said member when said one element is moved.

4. A device as in claim 2, said tube-like member being of a yieldable material to yieldably vary in cross section corresponding to the selected movement of said movable means.

5. A device as in claim 3, said movable elements extending for a substantial length of said tube-like member, and tip means on said device at the distal entry end thereof having said passage defined therein and being deformable to conform to the shape of the body opening.

6. A device as in claim 3, and deformable means on said device to enable the same to be conformed to the contour of the body opening.

7. A device for insertion into a body opening as an endotracheal tube and the like comprising a member for removable insertion into a body opening and having an outer surface for expanding toward engagement with and for contraction away from engagement with the body opening and an inner surface defining a passage in said member and that is open at the opposite ends of said member, said member including means movable to cause said member to expand and contract at its outer and inner surfaces along substantially the full length thereof and to vary the cross-sectional area of said passage, and operable means connected with said movable means to move the same to expand and contract said member.

8. A device as in claim 7, said member being of a yieldable material whose outer and inner surfaces have cross sections from which the same expand and to which the same normally contract.

9. A device as in claim 8, said yieldable material being initially formed with a memory of the cross section of the inner and outer surfaces and being expandable from said normal cross sections by the operation of said movable means and being returnable to said normal cross sections upon the termination of the operation of said movable means.

10. A device as in claim 8, said movable means being on said yieldable member between the inner and outer surfaces thereof.

11. A device as in claim 8, said member being deformable to conform to the contour of the body opening, and means on the entry distal end of said device being deformable to conform to the contour of the body opening.

12. An elongated substantially tube-like device for insertion into and removal from a body opening having an inner surface defining a passage extending from one end to the other end thereof and adapted to increase and decrease in its cross section at its inner and outer surfaces in a plane substantially perpendicular to the length thereof comprising a plurality of elements movable relative to each other in a direction substantially perpendicular to the length of said device and positioned along substantially the full length of said device and free of interference with said passage, means on said device to cause said elements to move relative to each other, and said device being an elastomeric member engaging said elements and movable therewith to increase and decrease in cross section in the plane substantially perpendicular to the length of said device in response to the relative movements of said elements.

13. A device as in claim 12, wherein the same has means deformable to conform to the contour of the body opening.

14. A device as in claim 13, said plurality of elements including at least two elongated elements and movable links connected therebetween.

15. A device as in claim 14, said deformable means being at the distal entry end of said device.

16. A device for use in a body opening comprising an elongated member having an essentially smooth uninterrupted outer surface for insertion into a body opening and having an inner surface defining a hollow, unobstructed through passage, said member being expandable along substantially its full length in a direction substantially normal to its length and having means operable to cause said outer and inner surfaces and said unobstructed through passage to expand in a direction substantially normal to the length of said member, and manual means on said device to operate said operable means.

17. A device as in claim 16, said member being of an elastomeric material expandable from an unexpanded condition to which the same normally tends to return.

18. A device as in claim 17, said operable means being on said member remote from the outer surface thereof.

19. A device as in claim 18, deformable means on said device on at least the end thereof to first enter the body opening and deformable to the contour of such opening.

20. A device as in claim 18, said operable means extending for at least a portion of the length of said member and including means to connect the same with said manual means.

* * * * *